US012808857B2

(12) United States Patent
Masago et al.

(10) Patent No.: US 12,808,857 B2
(45) Date of Patent: Nov. 24, 2026

(54) SENSOR DEVICE, OBJECT DETECTION METHOD, AND OBJECT DETECTION PROGRAM

(71) Applicant: OMRON CORPORATION, Kyoto (JP)

(72) Inventors: Hiroyasu Masago, Kyoto (JP); Kota Yukizane, Kyoto (JP); Daiki Ando, Kyoto (JP)

( * ) Notice: Subject to any disclaimer, the term of this patent is extended or adjusted under 35 U.S.C. 154(b) by 67 days.

(21) Appl. No.: 19/033,583

(22) Filed: Jan. 22, 2025

(65) Prior Publication Data

US 2025/0251385 A1 Aug. 7, 2025

(30) Foreign Application Priority Data

Feb. 6, 2024 (JP) ................................ 2024-016645

(51) Int. Cl.
*G01N 21/25* (2006.01)
*G01N 21/29* (2006.01)
*G01N 33/28* (2006.01)

(52) U.S. Cl.
CPC ....... *G01N 33/2888* (2013.01); *G01N 21/255* (2013.01); *G01N 21/293* (2013.01); *G01N 2201/0621* (2013.01)

(58) Field of Classification Search
CPC ........ G01J 3/501; G01J 3/513; G01N 21/251; G01N 21/255; G01N 21/293; G01N 2201/0621; G01N 33/2888
See application file for complete search history.

(56) References Cited

U.S. PATENT DOCUMENTS

| | | | | |
|---|---|---|---|---|
| 4,464,054 A * | 8/1984 | Karras | .................. | G01J 3/0218 356/406 |
| 6,225,974 B1 * | 5/2001 | Marsden | .............. | H04N 1/6058 345/590 |
| 2014/0146307 A1 * | 5/2014 | Arrondo | ................ | G01N 21/25 356/70 |
| 2023/0133321 A1 * | 5/2023 | Ishihara | .................... | G06F 3/14 356/402 |

FOREIGN PATENT DOCUMENTS

JP 2011-106875 A 6/2011

* cited by examiner

*Primary Examiner* — Hina F Ayub
(74) *Attorney, Agent, or Firm* — METROLEX IP LAW GROUP, PLLC; Robert L. Scott, Esq.

(57) ABSTRACT

A sensor device 10 includes a light projection unit 14, a light reception unit 15, an RGB value acquisition unit 22, a color index value calculation unit 24, and a determination unit 16. The light projection unit 14 projects light. The light reception unit 15 detects reflected light from an area illuminated with the light projected from the light projection unit 14. The RGB value acquisition unit 22 acquires color information about an object present in the illumination area on the basis of the reflected light detected by the light reception unit 15. The color index value calculation unit 24 calculates a single color index value on the basis of the R value, G value, and B value included in the color information acquired by the RGB value acquisition unit 22. The determination unit 16 compares the color index value calculated by the color index value calculation unit 24 with a specific threshold value to determine whether or not an object has been detected.

9 Claims, 9 Drawing Sheets

| | R VALUE | G VALUE | B VALUE | COLOR INDEX VALUE |
|---|---|---|---|---|
| FRESH LUBRICATING OIL | 1.237 | 1.091 | 0.536 | 5.49 |
| DETERIORATED LUBRICATING OIL (TO BE REPLACED) | 0.840 | 0.339 | 0.023 | 1.08 |

FIG. 6

SENSOR DEVICE, OBJECT DETECTION METHOD, AND OBJECT DETECTION PROGRAM

CROSS-REFERENCE TO RELATED APPLICATIONS this application claims priority to Japanese Patent Application No. 2024-016645 filed on Feb. 6, 2024. the entire disclosure of Japanese Patent Application No. 2024-016645 is hereby incorporated herein by reference.

BACKGROUND

Technical Field

The present invention relates to a sensor device, an object detection method, and an object detection program with which an object is detected using color information.

Description of the Related Art

For example, deterioration of lubricating oil used in a machine tool can lead to breakdown of the machine tool, so color sensors are used to monitor the color of the lubricating oil to sense its deterioration status.

For instance, Patent Literature 1 discloses a color sensor that includes three light-receiving elements that have transmission spectral sensitivity characteristics for each of the RGB colors and generate a photocurrent whose magnitude is proportional to the amount of light received, a switching circuit that selects the photocurrent, an A/D converter that converts the selected photocurrent into a digital signal, a register that holds digital values from the A/D converter, and a serial interface circuit that outputs the held digital values via terminals SCL and SDA.

CITATION LIST

Patent Literature

Patent Literature 1: JP-A 2011-106875

SUMMARY

Problem to be Solved by the Invention

However, the following problem is encountered with the conventional color sensor mentioned above.

That is, with the color sensor disclosed in the above publication, it is necessary to process data of three colors (R, G, and B values) to distinguish color differences, so for a detection object in which the three colors change simultaneously, it is difficult to set a threshold value for judging color differences due to the difference in the amount of light reflected from the detection object and the information processing of the three colors. Accordingly, in the case where the threshold value is not set properly, it is difficult to judge the colors very accurately.

It is an object of the present invention to provide a sensor device, an object detection method, and an object detection program with which a determination threshold value can be easily set, thereby improving user convenience.

Means for Solving Problem

The sensor device according to the first invention includes a light projection unit, a light reception unit, a color information acquisition unit, a color index value calculation unit, and a determination unit. The light projection unit projects light. The light reception unit detects reflected light from an area illuminated with light projected from the light projection unit. The color information acquisition unit acquires color information about an object present in the illumination area on the basis of the reflected light detected by the light reception unit. The color index value calculation unit calculates a single color index value on the basis of the R value, G value, and B value included in the color information acquired by the color information acquisition unit. The determination unit compares the color index value calculated by the color index value calculation unit with a specific threshold value to determine whether or not an object has been detected.

Here, whether or not an object such as deteriorated lubricating oil has been detected is determined on the basis of the results of a comparison between a threshold value and a single color index value calculated on the basis of the R value, G value, and B value included in the color information of the reflected light of light projected onto the object.

Here, the object is something for which a color-based determination is to be made by the sensor device, and may be in the form of either a solid, a liquid, or a gas.

The color index value is calculated from color information (RGB values) about an object obtained from reflected light, and is a numerical value that indicates the degree of color set on a scale from 0 to 10, for example, with achromatic colors (white, black, and gray) showing a high value and chromatic colors (red, green, and blue) showing a low value.

Determination based on color is, for example, a determination of the state of deterioration of a lubricating oil (object) used in a machine tool, and in the case where the calculated color index value is at or below a threshold value, the lubricating oil is judged to have deteriorated.

This makes it easier to judge an object by comparing a single color index value calculated from the R, G, and B values with a preset threshold value, than with a conventional method of performing color difference determination using the R, G, and B values.

As a result, a determination threshold value can be set more easily, thereby improving user convenience.

The sensor device according to the second invention is the sensor device according to the first invention, further comprising an RGB value correction unit that corrects the color information acquired by the color information acquisition unit.

This allows the accuracy of the above-mentioned color determination to be improved by obtaining RGB correction values that have been corrected so as to eliminate variance in the amount of light projected and variance in the light reception sensitivity attributable to individual differences in the light projection unit and the light reception unit, for example.

The sensor device according to the third invention is the sensor device according to the second invention, wherein the RGB value correction unit corrects the RGB values so that the RGB values when an achromatic object is detected are 1:1:1, respectively.

This allows the accuracy of the above-mentioned color determination to be improved by correcting the color information so that the R, G, and B values are 1:1:1, which is what they should be when an object that is achromatic (white, black, gray, etc.) is detected.

The sensor device according to the fourth invention is the sensor device according to the first or second invention, wherein the color index value calculation unit calculates the color index value on the basis of the R value, the G value, and the B value corrected by the RGB value correction unit.

This allows the accuracy of the determination to be improved by performing the above-mentioned color determination using a color index value calculated using an RGB correction value that has been corrected so as to eliminate variance in the amount of light projected and variance in the light reception sensitivity attributable to individual differences in the light projection unit and the light reception unit, for example.

The sensor device according to the fifth invention is the sensor device according to the first or second invention, further comprising a threshold storage unit that stores threshold values used by the determination unit in determining the object.

This allows an object to be judged using the threshold values stored in the threshold value storage unit.

The sensor device according to the sixth invention is the sensor device according to the second or third invention, further comprising a correction value storage unit that stores the correction values used in the RGB value correction unit.

Consequently, the correction values stored in the correction value storage unit can be used to correct the color information acquired by the color information acquisition unit.

The sensor device according to the seventh invention is the sensor device according to the first or second invention, further comprising a determination result storage unit that stores the determination result of the determination unit.

Consequently, the determination results stored in the determination result storage unit can be displayed on the display of a PC (personal computer), for example.

The sensor device according to the eighth invention is the sensor device according to the first or second invention, further comprising a communication unit that communicates the determination result of the determination unit to an external device including the object.

Consequently, in the case of monitoring changes in the color of a lubricating oil using a sensor device provided to a machine tool or the like, for example, whether or not there is a change in the color of the lubricating oil (whether or not the color index value is above a threshold value) can be transmitted to the machine tool, etc. as a determination result, allowing the user to easily grasp the deterioration state of the lubricating oil on a monitor screen of the machine tool, etc.

The sensor device according to the ninth invention is the sensor device according to the first or second invention, wherein the object is deteriorated oil.

This allows the deterioration of lubricating oil used in a machine tool or the like to be detected with high accuracy by comparing a single color index value with a threshold value, and prompting the user to replace the oil.

The object detection method according to the tenth invention includes a light projection step, a light reception step, a color information acquisition step, a color index value calculation step, and a determination step. The light projection step involves projecting light. The light reception step involves detecting reflected light from an area illuminated by the light projected in the light projection step. The color information acquisition step involves acquiring color information about an object present in the illumination area on the basis of the reflected light detected in the light reception step. The color index value calculation step involves calculating a single color index value on the basis of the R value, the G value, and the B value included in the color information acquired in the color information acquisition step. The determination step involves comparing the color index value calculated in the color index value calculation step with a specific threshold value to determine whether or not an object has been detected.

Here, it is determined whether or not an object such as deteriorated lubricating oil has been detected on the basis of the results of a comparison between a threshold value and a single color index value calculated on the basis of the R value, G value, and B value included in the color information for the reflected portion of the light projected onto the object.

Here, the object is something for which a color-based determination is to be made by the sensor device, and may be in the form of either a solid, a liquid, or a gas.

The color index value is calculated from the color information (RGB values) for the object obtained from reflected light, and is a numerical value that indicates the degree of color set on a scale from 0 to 10, for example, with achromatic colors (white, black, and gray) showing a high value and chromatic colors (red, green, and blue) showing a low value.

Determination based on color is, for example, a determination of the state of deterioration of a lubricating oil (object) used in a machine tool, and in the case where the calculated color index value is at or below a threshold value, the lubricating oil is judged to have deteriorated.

This makes it easier to judge an object by comparing a single color index value calculated from the R, G, and B values with a preset threshold value, than with a conventional method of performing color difference determination using the R, G, and B values.

As a result, a determination threshold value can be set more easily, thereby improving user convenience.

The object detection program according to the eleventh invention causes a computer to execute an object detection method including a light projection step, a light reception step, a color information acquisition step, a color index value calculation step, and a determination step. The light projection step involves projecting light. The light reception step involves detecting reflected light from an area illuminated by the light projected in the light projection step. The color information acquisition step involves acquiring color information about an object present in the illumination area on the basis of the reflected light detected in the light reception step. The color index value calculation step involves calculating a single color index value on the basis of the R value, the G value, and the B value included in the color information acquired in the color information acquisition step. The determination step involves comparing the color index value calculated in the color index value calculation step with a specific threshold value to determine whether or not an object has been detected.

Here, it is determined whether or not an object such as deteriorated lubricating oil has been detected on the basis of the results of a comparison between a threshold value and a single color index value calculated on the basis of the R value, G value, and B value included in the color information for the reflected portion of the light projected onto the object.

Here, the object is something for which a color-based determination is to be made by the sensor device, and may be in the form of either a solid, a liquid, or a gas.

The color index value is calculated from the color information (RGB values) for the object obtained from reflected light, and is a numerical value that indicates the degree of color set on a scale from 0 to 10, for example, with achromatic colors (white, black, and gray) showing a high value and chromatic colors (red, green, and blue) showing a low value.

Determination based on color is, for example, a determination of the state of deterioration of a lubricating oil (object) used in a machine tool, and in the case where the calculated color index value is at or below a threshold value, the lubricating oil is judged to have deteriorated.

This makes it easier to judge an object by comparing a single color index value calculated from the R, G, and B values with a preset threshold value, than with a conventional method of performing color difference determination using the R, G, and B values.

As a result, a determination threshold value can be set more easily, thereby improving user convenience.

(Effects)

With the sensor device according to the present invention, a determination threshold can be easily set, and this improves user convenience.

BRIEF DESCRIPTION OF THE DRAWINGS

FIG. 6 is a diagram showing RGB values and color index values corresponding to new lubricating oil and deteriorated waste oil;

DETAILED DESCRIPTION OF THE EMBODIMENT

The sensor device according to an embodiment of the present invention will now be described with reference to FIGS. 1 to 7.

In this embodiment, some unnecessarily detailed description may be omitted. For example, detailed description of already known facts or redundant description of components that are substantially the same may be omitted. This is to avoid unnecessary repetition in the following description, and facilitate an understanding on the part of a person skilled in the art.

The applicant has provided the appended drawings and the following description so that a person skilled in the art might fully understand this disclosure, but does not intend for these to limit what is discussed in the patent claims.

(1) Configuration of Sensor Device 10

The sensor device 10 according to this embodiment is provided to a machine tool, for example, and determines the deterioration state of the lubricating oil by monitoring changes in the color of the lubricating oil (object) used in the machine tool.

Figure 1:
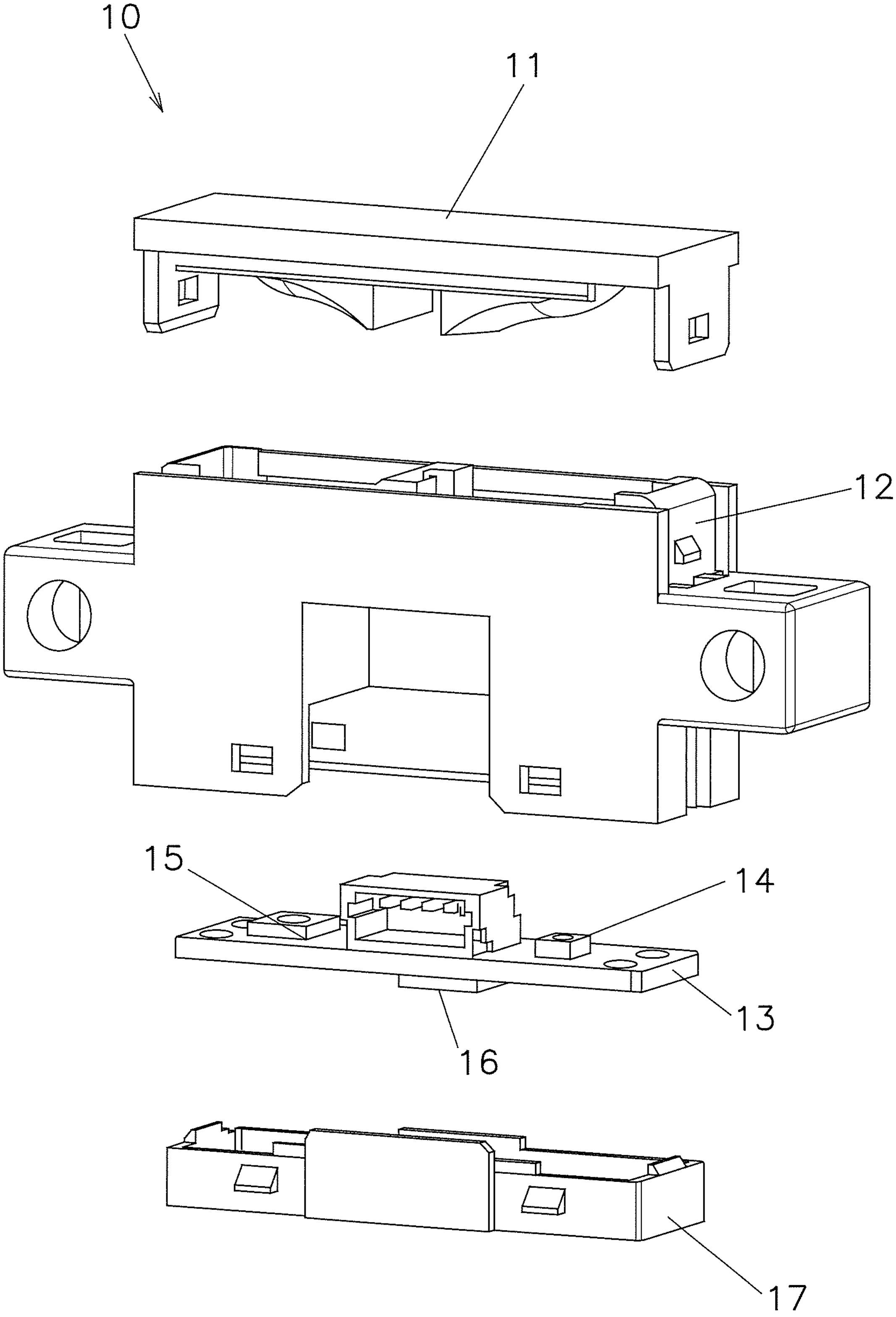
FIG. 1 is an exploded oblique view of the configuration of the sensor device according to an embodiment of the present invention.

As shown in FIG. 1, the sensor device 10 includes a lens 11, a case 12, a substrate 13, a light projection unit 14, a light reception unit 15, a determination unit 16, and a cover 17.

The lens 11 is attached to the case 12 and transmits light emitted from the light projection unit 14 disposed inside the case 12, directing the light toward an object such as lubricating oil, and transmits light reflected from the surface of the object so that this light will be received by the light reception unit 15.

The case 12 is a substantially box-shaped member and envelops the substrate 13 on which the light projection unit 14 and the light reception unit 15 are mounted.

The substrate 13 is contained within the case 12, and the light projection unit 14 and the light reception unit 15 are disposed on the surface on the lens 11 side.

The light projection unit 14 is a light source such as an LED (light emitting diode), and projects light onto an object, such as lubricating oil, through the lens 11.

The light reception unit 15 receives, via the lens 11, the light that has been emitted from the light projection unit 14, transmitted through the object, reflected by the reflecting plate 18, and transmitted through the object again.

The determination unit 16 uses a single color index value calculated on the basis of the R value, G value, and B value included in the color information for the reflected light received by the light reception unit 15, to determine whether or not an object (deteriorated lubricating oil) has been detected. The determination processing performed by the determination unit 16 will be described in detail below.

The cover 17 is attached to the case 12 and covers the end on the opposite side from the lens 11.

Figure 2:
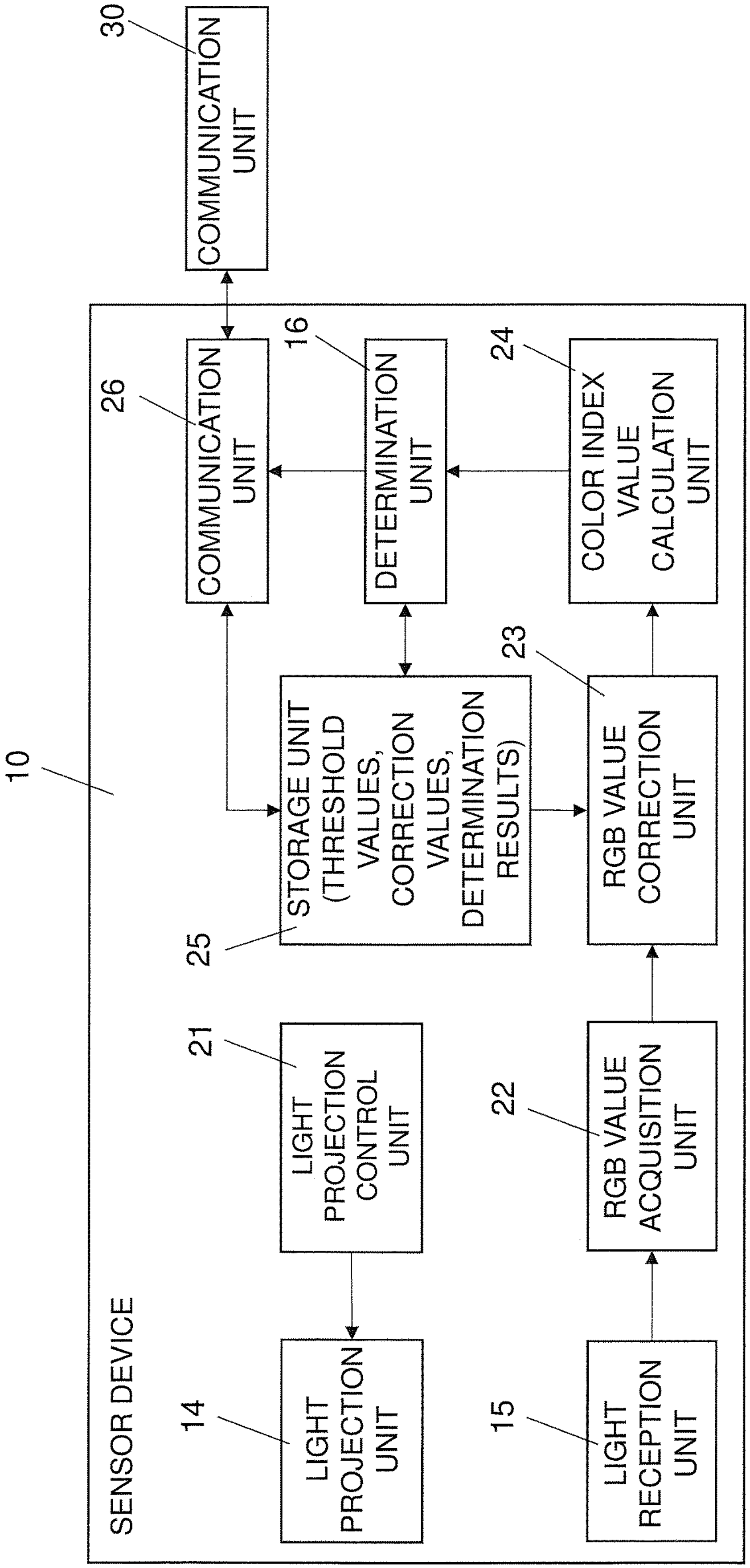
FIG. 2 is a control block diagram of the sensor device in FIG. 1.

As shown in FIG. 2, the sensor device 10 includes the above-mentioned light projection unit 14 and light reception unit 15, the determination unit 16, a light projection control unit 21, an RGB value acquisition unit (color information acquisition unit) 22, an RGB value correction unit 23, a color index value calculation unit 24, a memory unit (threshold memory unit, correction value memory unit, determination result memory unit) 25, and a communication unit 26.

The determination unit 16 compares the color index value calculated by the color index value calculation unit 24 (discussed below) with a specific threshold value to determine whether or not an object has been detected.

The light projection control unit 21 controls the light projection unit 14 that illuminates an object such as lubricating oil with light.

The RGB value acquisition unit (color information acquisition unit) 22 acquires color information about an object present in the illumination area on the basis of the reflected light detected by the light reception unit 15.

The RGB value correction unit 23 corrects the color information acquired by the RGB value acquisition unit 22. More precisely, the RGB value correction unit 23 corrects the RGB values so that the RGB values when an achromatic (white, black, or gray) object has been detected will be 1:1:1, respectively.

The color index value calculation unit 24 calculates a single color index value based on the R value, the G value, and the B value included in the color information acquired by the RGB value acquisition unit 22. More precisely, the color index value calculation unit 24 calculates the color index value on the basis of the R value, the G value, and the B value corrected by the RGB value correction unit 23.

The memory unit (threshold memory unit, correction value memory unit, determination result memory unit) 25 stores the threshold values used to judge the object in the determination unit 16, the correction values used in the RGB value correction unit 23, and the determination results in the determination unit 16.

The communication unit 26 communicates the determination result produced by the determination unit 16 to an external device such as a machine tool that includes an object such as lubricating oil.

The communication unit 30 is provided to a machine tool on which the sensor device 10 is mounted, for example, and receives the determination result from the sensor device 10.

Figure 3B:
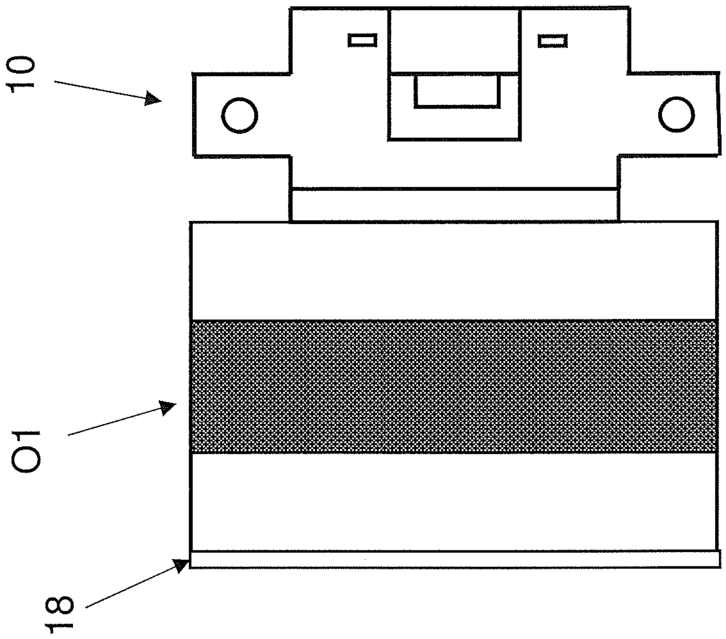
FIG. 3B is a conceptual diagram showing a state in which the sensor device in FIG. 1 is used to monitor the change in color of the lubricating oil after deterioration.
Figure 3A:
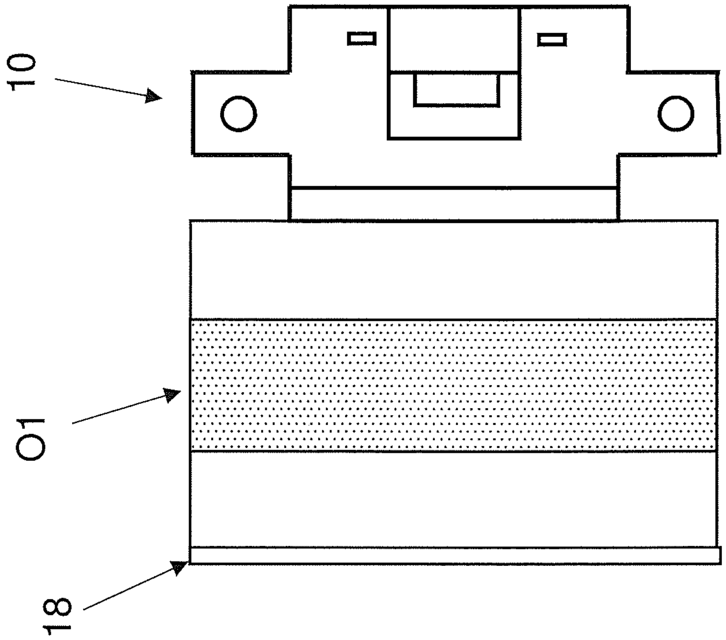
FIG. 3A is a conceptual diagram showing a state in which the sensor device in FIG. 1 is used to monitor the change in color of a lubricating oil before deterioration.

More precisely, as shown in FIGS. 3A and 3B, the sensor device 10 irradiates the lubricating oil O1 circulating inside the machine tool with light and receives the light reflected by the reflecting plate 18 to monitor the degree of deterioration of the lubricating oil. That is, the sensor device 10 uses the property of the lubricating oil of changing from a light brown color (see FIG. 3A) to dark brown (see FIG. 3B) as deterioration progresses, to calculate a single color index value from the color information (R value, G value, and B value) of the reflected light, and in the case where it the value is determined to be below a specific threshold value, it determines that the lubricating oil is deteriorating and displays a message, etc., to prompt replacement, as shown in FIG. 3B.

This allows the degree of deterioration of the lubricating oil to be monitored on a monitor device or the like on the machine tool side, and in the event that the color index value of the lubricating oil falls below the specific threshold, it is determined that the lubricating oil has deteriorated and the user of the machine tool can be notified that it is time to change the lubricating oil.

Here, detection of deteriorated lubricating oil that needs to be replaced is performed by utilizing the fact that in a state in which the lubricating oil is fresh, such as immediately after its replacement, the color index value is close to achromatic and therefore high, and as deterioration progresses, this value starts changing to a lower value close to being chromatic.

Figure 5:
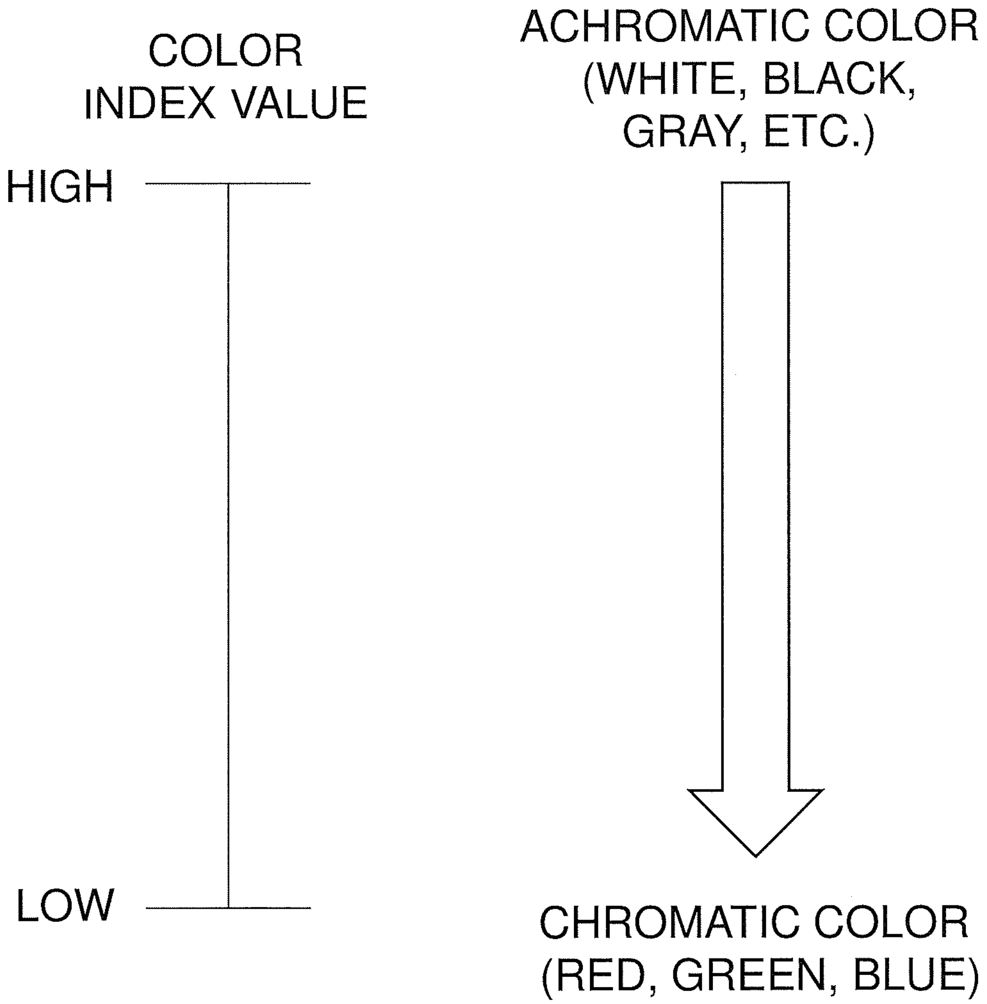
FIG. 5 is a diagram of the relation between high and low color index values and achromatic and chromatic colors.

The color index value used for the determination is a single value calculated from the color information (R value, G value, and B value) about the light coming from the object, and as shown in FIG. 5, achromatic colors (white, black, and gray) have higher values and chromatic colors (red, green, and blue) have lower values.

Figure 4:
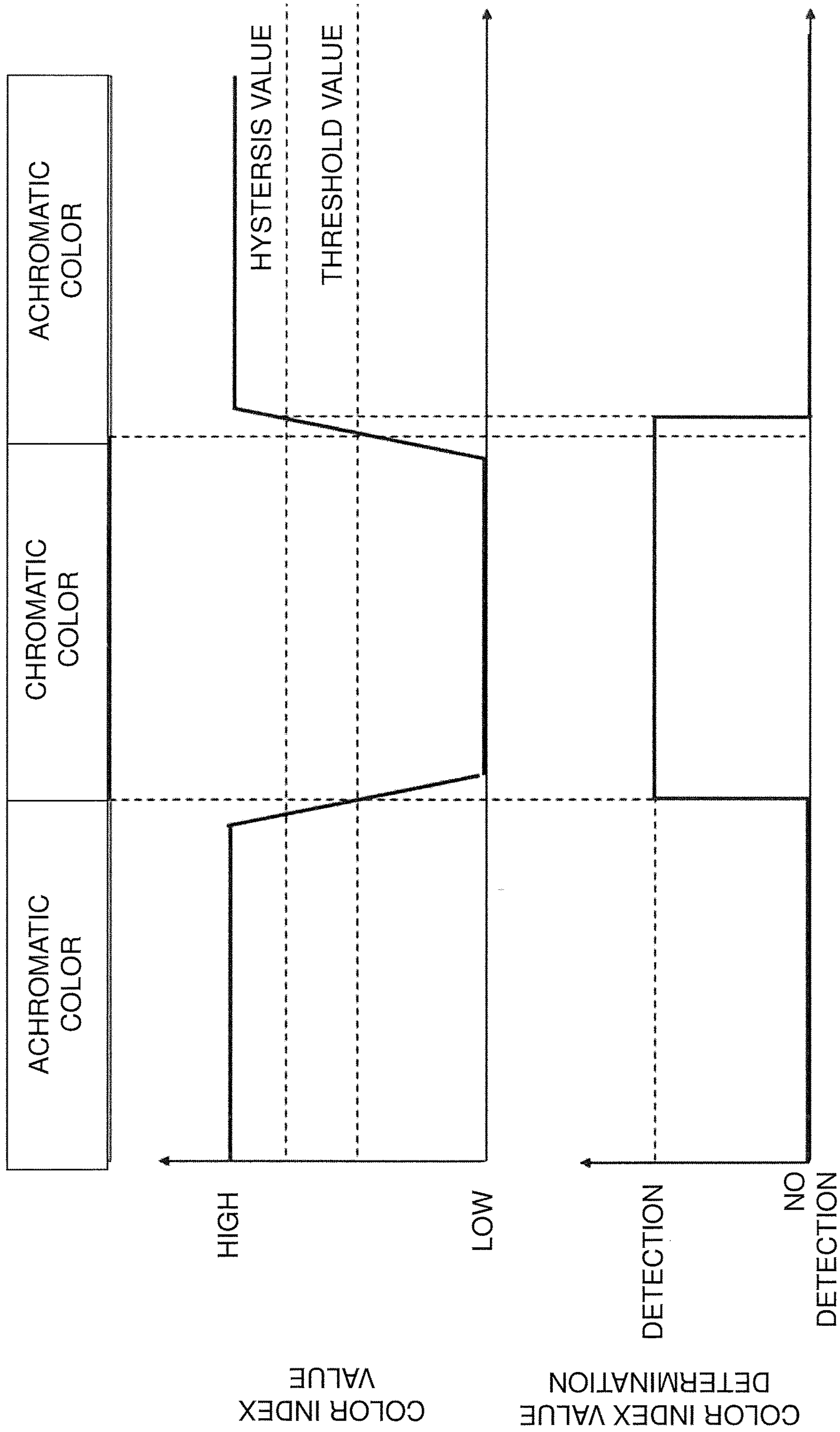
FIG. 4 is a graph of the relation between the change in color (achromatic/chromatic), the color index value, and the determination result (detected/undetected)

That is, in the case where the lubricating oil deteriorates and the color index value decreases, the color of the lubricating oil starts changing from achromatic to chromatic, as shown in FIG. 4. Therefore, the determination unit 16 detects that the color index value calculated from the color information for the lubricating oil has dropped below the specific threshold value, and determines that the object (lubricating oil that has deteriorated to the point where it needs replacing) has been detected.

In the event that the color of the object changes from a chromatic color to an achromatic color, as shown in FIG. 4, once the color index value reaches or exceeds a preset hysteresis value, it is determined that the object has not been detected.

More specifically, as shown in FIG. 6, in the case of fresh lubricating oil immediately after replacement, the R value is 1.237, the G value is 1.091, and the B value is 0.536. The color index value calculated from these R, G, and B values is 5.49.

On the other hand, as shown in FIG. 6, in the case of lubricating oil that has been used in a machine tool and has deteriorated (oil that is to be replaced), the R value is 0.840, the G value is 0.339, and the B value is 0.023. The color index value calculated from these R, G, and B values is 1.08.

As discussed above, the color index value of fresh lubricating oil immediately after replacement is high, while the color index value of lubricating oil that has deteriorated is lower.

Here, the color index value C can be calculated from the color information (R value, G value, and B value) using the following relational expression (1), for example.

Mathematical Formula 1

$$C=\sqrt{R^2+G^2+B^2} \tag{1}$$

This relational expression is merely an example of a means for calculating the color index value C, and the present invention is not necessarily limited to this.

Also, chattering during determination of the change in color of the lubricating oil O1 (from achromatic to chromatic) can be prevented by setting a hysteresis value for the color index value C used in the determination.

More specifically, under the condition of hysteresis value≥determination threshold, in the case where the color index value C≤determination threshold, it is determined that there is a change from undetected to detected, and in the case where the color index value C> hysteresis value, it is determined that there is a change from detected to undetected.

On the other hand, under the condition of hysteresis value<determination threshold, in the case where the color index value C≥determination threshold, it is determined that there is a change from undetected to detected, and in the case where the color index value C<hysteresis value, it is determined that there is a change from detected to undetected.

Object Detection Method

Figure 7:
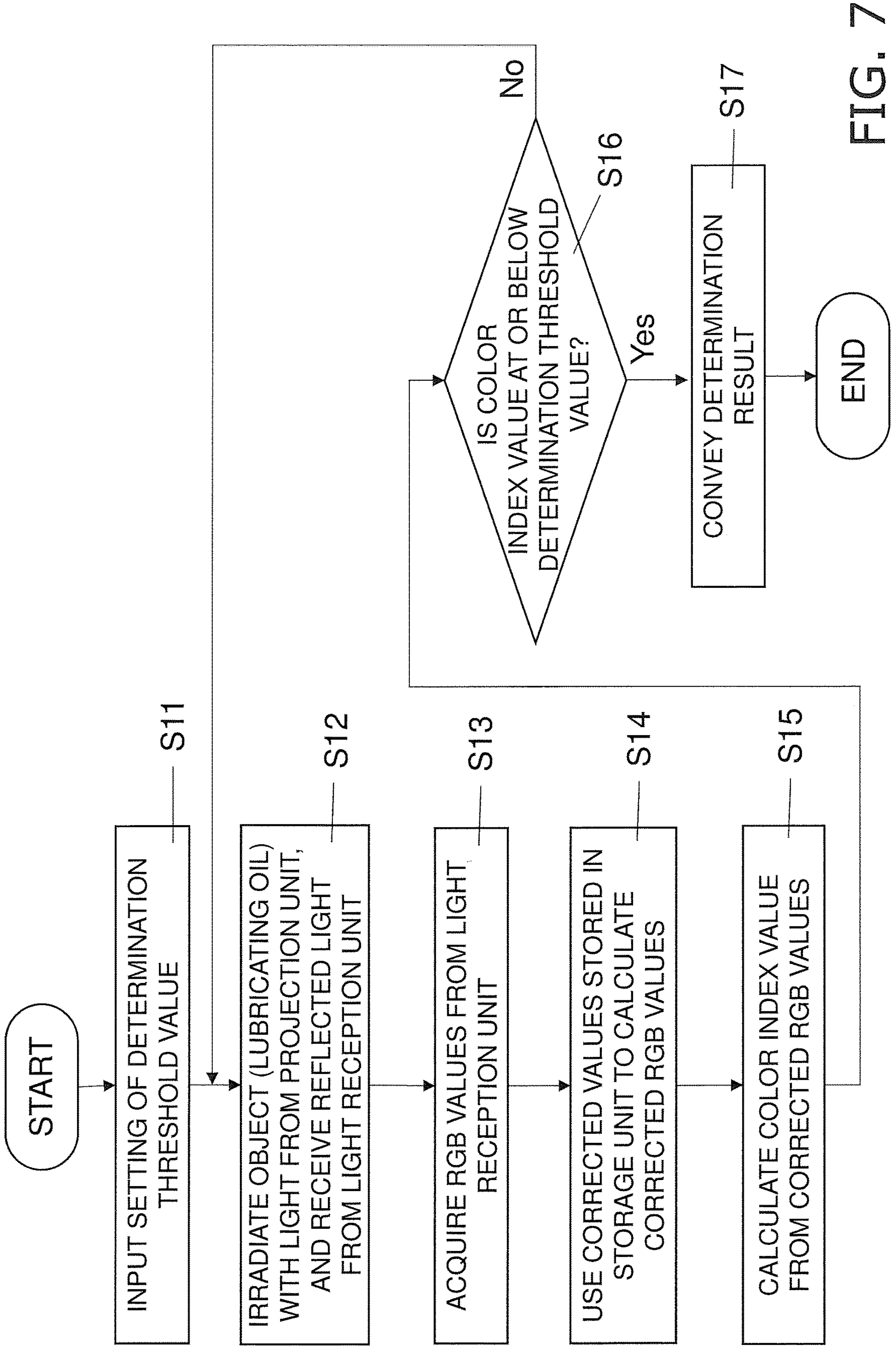
FIG. 7 is a flowchart of the flow of processing in an object detection method performed by the sensor device in FIG. 2.

The sensor device 10 of this embodiment performs an object detection method as shown in the flowchart in FIG. 7.

That is, in step S11, the user of a machine tool inputs a setting value for a determination threshold for determining the extent of deterioration of the lubricating oil.

Next, in step S12, the light projection control unit 21 controls the light projection unit 14 to project light onto the target (lubricating oil), and the light reception unit 15 receives the reflected light.

Next, in step S13, the RGB value acquisition unit 22 acquires color information (RGB values) about the light received by the light reception unit 15.

Next, in step S14, the RGB value correction unit 23 uses the correction values stored in the storage unit 25 to calculate corrected RGB values. The calculation of the corrected RGB values is performed so that the R value, G value, and B value become 1:1:1 in the case where reflected light from an achromatic object is received, for example.

Next, in step S15, the color index value calculation unit 24 calculates a color index value from the RGB correction values calculated by the RGB value correction unit 23.

Here, the color index value C is calculated using the relational expression shown in the above-mentioned Mathematical Formula 1, for example.

Next, in step S16, the determination unit 16 determines whether or not the color index value C calculated by the color index value calculation unit 24 is at or below the determination threshold value stored in the storage unit 25. If the calculated color index value C is at or below the threshold value, it is determined that the lubricating oil has deteriorated and its color has changed to a chromatic color, and the processing proceeds to step S17, whereas if the calculated color index value C is above the threshold value, it is determined that the lubricating oil has not yet deteriorated and its color remains close to an achromatic color, and the processing returns to step S12.

Next, in step S17, since it was determined in step S16 that the color index value C was at or below the threshold value and that the lubricating oil had deteriorated and changed to a chromatic color, the communication unit 26 conveys the determination result.

This allows a message indicating that the lubricating oil has deteriorated and needs to be replaced, or the like, to be displayed on the display screen of the machine tool, for example.

Main Features

As shown in FIG. 2, the sensor device 10 of this embodiment includes the light projection unit 14, the light reception unit 15, the RGB value acquisition unit 22, the color index value calculation unit 24, and the determination unit 16. The light projection unit 14 projects light. The light reception unit 15 detects reflected light from an area illuminated by the light projected from the light projection unit 14. The RGB value acquisition unit 22 acquires color information about an object present in the illumination area on the basis of the reflected light detected by the light reception unit 15. The color index value calculation unit 24 calculates a single color index value on the basis of the R value, G value, and B value included in the color information acquired by the RGB value acquisition unit 22. The determination unit 16 compares the color index value calculated by the color index value calculation unit 24 with a specific threshold value to determine whether or not an object has been detected.

Consequently, compared to a conventional method in which the R, G, and B values are used to perform color difference determination, there is no need to set a threshold value for each of the R, G, and B values, and the object can be easily judged by comparing a single color index value with a preset threshold value.

As a result, it is easier to set the threshold value used for determination, thereby improving user convenience.

OTHER EMBODIMENTS

An embodiment of the present invention was described above, but the present invention is not limited to or by the above embodiment, and various modifications are possible without departing from the gist of the invention.

(A)

In the above embodiment, an example was given in which the present invention was realized as a sensor device and an object detection method, but the present invention is not limited to this.

For example, the present invention may be realized as an object detection program that causes a computer to execute the object detection method described above.

This object detection program is stored in a memory (storage unit) provided to the sensor device, and a CPU reads the object detection program stored in the memory and causes the hardware to execute the various steps. More specifically, the CPU reads the object detection program and executes the above-mentioned light projection step, light reception step, color information acquisition step, color index value calculation step, and determination step, which yields the same effect as what was described above.

Also, the present invention may be realized as a recording medium on which an object detection program is stored.

(B)

In the above embodiment, an example was given in which corrected R, G, B values obtained by correcting the R, G, and B values acquired in the RGB value acquisition unit (color information acquisition unit) 22 were used to calculate a color index value. However, the present invention is not limited to this.

For example, in the case where there is no need to take into account the decrease in accuracy attributable to individual differences between the light projection unit and the light reception unit, the configuration may be such that the R, G, and B values acquired by the color information acquisition unit are used to calculate the color index value, without correcting the R, G, and B values.

(C)

In the above embodiment, an example was given in which the change in the color of an object (lubricating oil) having a color index value close to an achromatic color was monitored, and a change to a color close to a chromatic color was detected to determine the extent of deterioration of the lubricating oil, but the present invention is not limited to this.

For example, the extent of deterioration of the object may be determined by detecting that an object close to a chromatic color has deteriorated and has changed to a color that is close to achromatic.

(D)

In the above embodiment, an example was given in which the user set and inputted a determination threshold value for determining the extent of deterioration of a lubricating oil, but the present invention is not limited to this.

For example, in the case where the object is constant, the determination may make use of a color index value and a preset determination threshold value.

(E)

In the above embodiment, an example was given in which the determination result produced by the determination unit 16 was transmitted from the communication unit 26 on the sensor device 10 side to the communication unit 30 on the machine tool side, and a message prompting replacement of the lubricating oil or the like was displayed on a display screen or the like on the machine tool side. However, the present invention is not limited to this.

For example, in addition to, or instead of, displaying a message prompting replacement of the lubricating oil due to deterioration or the like, an alarm sound or the like may be outputted to notify the user of the deterioration of the lubricating oil.

Even in this case, the user of the machine tool will recognize that the lubricating oil has deteriorated and can be prompted to replace the oil right away.

(F)

In the above embodiment, an example was given in which the sensor device of the present invention was applied as a device for monitoring the deterioration state of a lubricating oil used in a machine tool, etc. However, the present invention is not limited to this.

For example, in addition to monitoring the deterioration of lubricating oil, the sensor device of the present invention may be applied to various kinds of device for detecting a change in the color (color difference) of an object and performing various controls.

(G)

In the above embodiment, an example was given in which the sensor device 10 was a recursive reflection type, with which the light emitted from the light projection unit 14 was reflected by the reflecting plate 18 and the reflected light was received by the light reception unit 15. However, the present invention is not limited to this.

Figure 8:
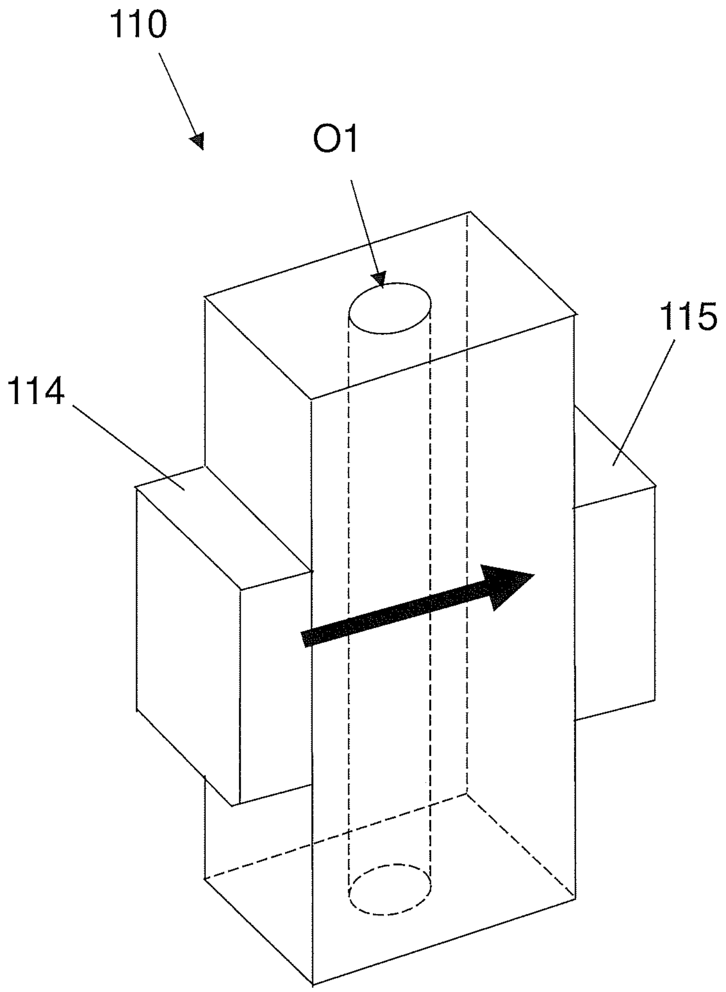
FIG. 8 is a schematic diagram of the configuration of a transmission type of sensor device according to another embodiment of the present invention.

For example, as shown in FIG. 8, a transmission type of sensor device 110 may be used, which includes a light projection unit 114 that emits light toward an object (such as a lubricating oil O1), and a light reception unit 115 that is disposed at a position opposite (coaxial with) the light projection unit 114 and receives light that has passed through the object (such as the lubricating oil O1) between the light projection unit 114 and the light reception unit 115, at the light reception unit 115.

Alternatively, for example, the sensor device may be configured as a solid detection sensor device, which detects an object such as a seam in a carrier tape, in which the reflected part of the light emitted from a light projection unit and irradiating an object is received by a light reception unit, and a change in color is detected.

(H)

In the above embodiment, an example was given in which the sensor device 10 detected a change in the color of the lubricating oil from an achromatic color to a chromatic color, but the present invention is not limited to this.

Figure 9:
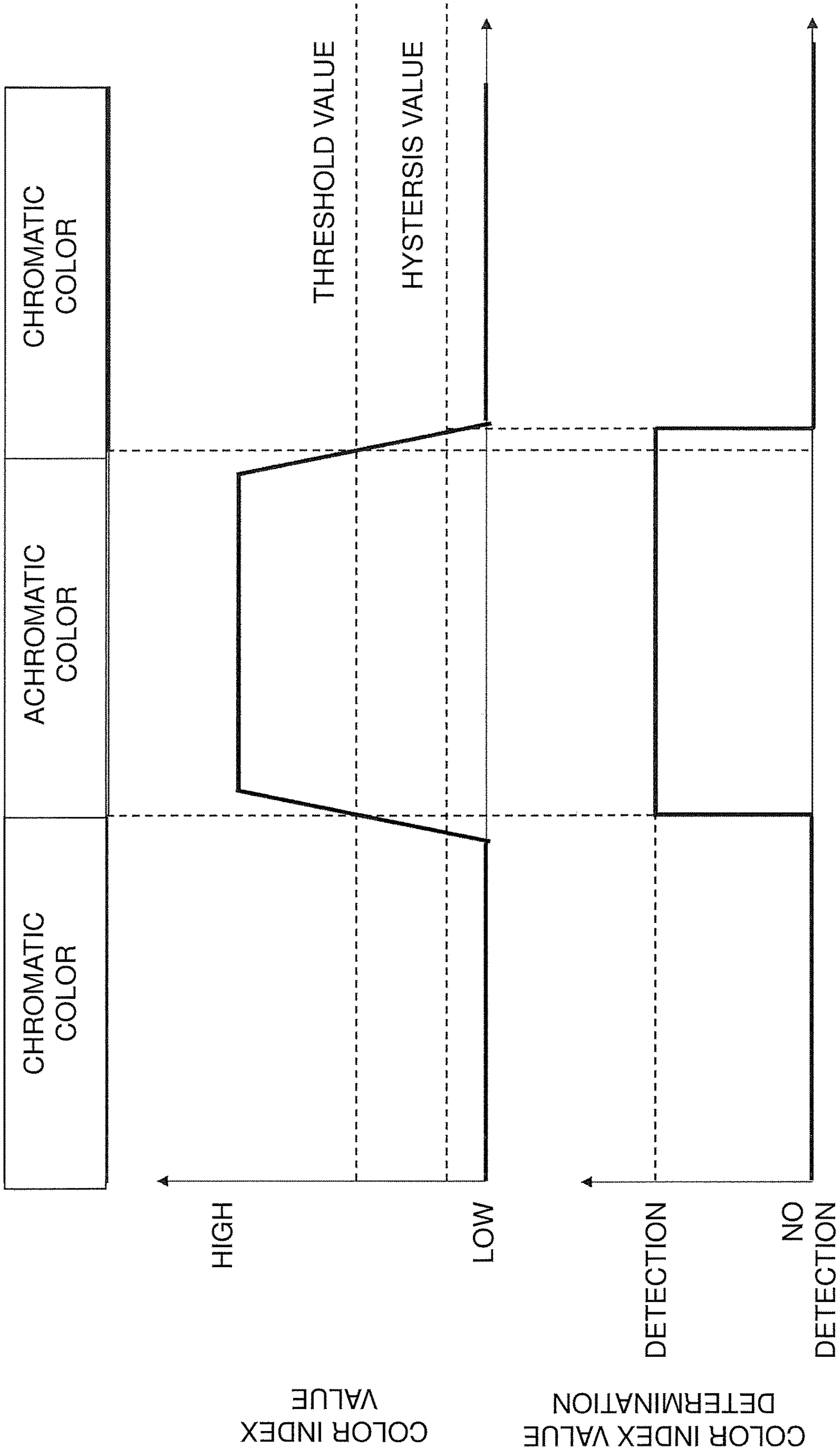
FIG. 9 is a graph of the relation between the change in color (achromatic/chromatic), color index value, and determination result (detected/undetected) in a sensor device according to yet another embodiment of the present invention.

For example, as shown in FIG. 9, the sensor device may be configured to detect a change in the color of an object from a chromatic color to an achromatic color.

Additions

The sensor device according to the first invention includes:

a light projection unit that projects light;

a light reception unit that senses the amount of reflected light received from an area illuminated with light projected from the light projection unit;

a color information acquisition unit that acquires color information about an object present in the illumination area on the basis of the amount of light received by the light reception unit;

a color index value calculation unit that calculates a single color index value on the basis of the R value, G value, and B value included in the color information acquired by the color information acquisition unit; and a determination unit that compares the color index value calculated by the color index value calculation unit with a specific threshold value to determine whether or not an object has been detected.

The sensor device according to the second invention is the sensor device according to the first invention, further comprising an RGB value correction unit that corrects the color information acquired by the color information acquisition unit.

The sensor device according to the third invention is the sensor device according to the second invention, wherein the RGB value correction unit corrects the RGB values so that the RGB values when an achromatic object is detected are 1:1:1, respectively.

The sensor device according to the fourth invention is the sensor device according to any of the first to third inventions, wherein the color index value calculation unit calculates the color index value on the basis of the R value, the G value, and the B value corrected by the RGB value correction unit.

The sensor device according to the fifth invention is the sensor device according to any of the first to fourth inventions, further comprising a threshold storage unit that stores threshold values used by the determination unit in determining the object.

The sensor device according to the sixth invention is the sensor device according to the second or third invention, further comprising a correction value storage unit that stores the correction values used in the RGB value correction unit.

The sensor device according to the seventh invention is the sensor device according to any of the first to sixth inventions, further comprising a determination result storage unit that stores the determination result of the determination unit.

The sensor device according to the eighth invention is the sensor device according to any of the first to seventh inventions, further comprising a communication unit that communicates the determination result of the determination unit to an external device including the object.

The sensor device according to the ninth invention is the sensor device according to any of the first to eighth inventions, wherein the object is deteriorated oil.

INDUSTRIAL APPLICABILITY

The sensor device of the present invention exhibits the effect of making it easier to set threshold values used for determination, thereby improving user convenience, and as such can be widely applied to devices that use color information to make various kinds of determination.

REFERENCE SIGNS LIST

10 sensor device
11 lens
12 case
13 substrate
14 light projection unit
15 light reception unit
16 determination unit
17 cover
18 reflecting plate
21 light projection control unit
22 RGB value acquisition unit (color information acquisition unit)
23 RGB value correction unit
24 color index value calculation unit
25 storage unit (threshold value storage unit, correction value storage unit, determination result storage unit)
26 communication unit
30 communication unit

What is claimed is:

1. A sensor device, comprising a light projection unit configured to project light;

a light reception unit configured to detect reflected light from an area illuminated with light projected from the light projection unit;

a color information acquisition unit configured to acquire color information about an object present in an illumination area on the basis of the reflected light detected by the light reception unit;

a color index value calculation unit configured to calculate a single color index value on the basis of R value, G value, and B value included in the color information acquired by the color information acquisition unit;

a determination unit configured to compare the color index value calculated by the color index value calculation unit with a specific threshold value to determine whether or not an object has been detected; and an RGB value correction unit configured to correct the color information acquired by the color information acquisition unit, wherein the RGB value correction unit corrects the RGB values so that the RGB values when an achromatic object is detected are 1:1:1, respectively.

2. The sensor device according to claim 1, wherein the color index value calculation unit calculates the color index value on the basis of the R value, the G value, and the B value corrected by the RGB value correction unit.

3. The sensor device according to claim 1, further comprising a threshold storage unit configured to store threshold values used by the determination unit in determining the object.

4. The sensor device according to claim 1, further comprising a correction value storage unit configured to store correction values used in the RGB value correction unit.

5. The sensor device according to claim 1, further comprising a determination result storage unit configured to store a determination result of the determination unit.

6. The sensor device according to claim 1, further comprising a communication unit configured to communicate a determination result of the determination unit to an external device including the object.

7. The sensor device according to claim 1, wherein the object is deteriorated oil.

8. An object detection method, comprising:

a light projection step of projecting light;

a light reception step of detecting reflected light from an area illuminated by the light projected in the light projection step;

a color information acquisition step of acquiring color information about an object present in an illumination area on the basis of the reflected light detected in the light reception step;

a color index value calculation step of calculating a single color index value on the basis of R value, G value, and B value included in the color information acquired in the color information acquisition step;

a determination step of comparing the color index value calculated in the color index value calculation step with a specific threshold value to determine whether or not an object has been detected, and an RGB value correction step of correcting the color information acquired in the color information acquisition step, wherein in the RGB value correction step, the RGB values are corrected so that the RGB values when an achromatic object is detected are 1:1:1, respectively.

9. A non-transitory, computer readable medium storing an object detection program that, when read and executed, causes a computer to execute an object detection method comprising the steps of:

a light projection step of projecting light;

a light reception step of detecting reflected light from an area illuminated by the light projected in the light projection step;

a color information acquisition step of acquiring color information about an object present in an illumination area on the basis of the reflected light detected in the light reception step;

a color index value calculation step of calculating a single color index value on the basis of R value, G value, and B value included in the color information acquired in the color information acquisition step; and a determination step of comparing the color index value calculated in the color index value calculation step with a specific threshold value to determine whether or not an object has been detected, and an RGB value correction step of correcting the color information acquired in the color information acquisition step, wherein in the RGB value correction step, the RGB values are corrected so that the RGB values when an achromatic object is detected are 1:1:1, respectively.

* * * * *